US005262306A

United States Patent [19]
Robeson et al.

[11] Patent Number: 5,262,306
[45] Date of Patent: Nov. 16, 1993

[54] METHODS FOR IDENTIFYING CERCOSPORIN-DEGRADING MICROORGANISMS

[76] Inventors: David J. Robeson, 7198 Emerald Ave., Dublin, Calif. 94568; Mahbubul A. F. Jalal, 755 Sunflower Dr., Lathrop, Calif. 95330; Robert B. Simpson, 226 Montego Dr., Danville, Calif. 94526

[21] Appl. No.: 503,829

[22] Filed: Apr. 3, 1990

Related U.S. Application Data

[63] Continuation-in-part of Ser. No. 412,980, Sep. 26, 1989, abandoned.

[51] Int. Cl.$^5$ .......................... C12Q 1/02; C12Q 1/04; C12N 1/38; C12N 1/12
[52] U.S. Cl. ......................................... 435/29; 435/34; 435/243; 435/244; 435/248; 435/249; 435/252.1; 435/252.5; 435/832; 435/839; 435/849; 435/876
[58] Field of Search .................... 435/29, 34, 243, 244, 435/252.1, 252.5, 253.3, 248, 249, 832, 839, 849, 876

[56] References Cited

U.S. PATENT DOCUMENTS 4,658,082  4/1987  Simpson et al. .

OTHER PUBLICATIONS

Daub, M. E., Hortscience 19(3):382–387 (Jun. 1984).
Assante et al., (1977) *Phytochemistry* 16:243–247.
Calpouzos (1966) *Ann. Rev. Phytopathology* 4:369–390.
Calpouzos, (1967) *Phytopathology* 57:799–800.
Daub, (1987) "The Fungal Photosynthesizer Cercosporin and its Role in Plant Disease in Light-Activated Pesticides" (Ed. J. R. Heitz & K. R. Downum), pp. 271–280, Amer. Chem. Soc., Washington D.C.
Hoekema et al., (1983) *Nature* 303:179–180.
Jenns et al., (1983) *Phytopathology* 79:213–219.
Kuyama et al., (1957) *J. Amer. Chem. Soc.* 79:5725–5726.
Lynch et al., (1979) *Trans. Br. Mycol. Soc.* 72:31–37.
Okubo et al., (1975) *Agric. Biol. Chem.* 39:1173–1175.
Simpson et al., (1986) *Plant Mol. Biol.* 6:403–415.
Yamazaki et al., (1972) *Agric. Biol. Chem.* 36:1707–1718.
Zambryski et al., (1983) *EMBO J.* 2:2143–2150.
Stavely et al., *Phytopathology* (1986) 58:1372–1376.
Yamazaki et al., *Agr. Biol. Chem.* (1975) 39(1):287–288.
Anzai et al., *Mol. Gen. Genet.* (1989) 219:492–494.

*Primary Examiner*—Margaret Moskowitz
*Assistant Examiner*—Stephanie W. Zitomer
*Attorney, Agent, or Firm*—Morrison & Foerster

[57] ABSTRACT

Methods for the isolation and purification of the phytotoxin cercosporin are disclosed as well as methods for identifying microorganisms capable of degrading cercosporin. Cercosporin can be purified from members of the fungal genus Cercospora and incorporated into culture medium for selection of those organisms resistant to cercosporin. Once identified, these organisms can be used to isolate the protein and the gene responsible for conferring cercosporin-resistance. The gene can be cloned and inserted into a suitable expression vector so that the protein can be further characterized. Additionally, the DNA encoding for cercosporin-resistance can be inserted into a vector suitable for transforming an Agrobacterium and the Agrobacterium in turn used to transform plant cells normally susceptible to Cercospora infection. Plants can be regenerated from the transformed plant cells. In this way, a transgenic plant can be produced with the capability of degrading cercosporin.

11 Claims, 2 Drawing Sheets

```
NACE agar culture (100%)
        |
cells (4.1%)
        |
        NACE agar (95.9%)
        | extract w/ 50% aqueous
        | acetone/EDTA [x3]
        |
agar (4.2%)
        |
        acetone/water (91.7%)
        | extract w/ ethyl acetate [x2]
        |
aqueous
fraction (44.5%)
        |
        ethyl acetate fraction (47.3%)
        | TLC
        |
polar
fraction (17.7%)
        |
        non-polar fraction (29.6%)
        (cercosporin)
```

*Cercospora beticola*
(cultured on PDA/continuous light/25°C/2-3 weeks)

↓ → discard colorless agar extract pigmented agar
0.5N NaOH (3x2 vols)

↓ → discard extracted agar partition acidified extract
against EtOAc

↓ → discard aqueous phase pool organic phases &
reduce to dryness

↓

Sephadex LH20 column chromatography

↓ pool cercosporin fractions

↓ crystallize/EtOH

↓ pure cercosporin

FIGURE 1

METHODS FOR IDENTIFYING CERCOSPORIN-DEGRADING MICROORGANISMS

CROSS-REFERENCE TO RELATED APPLICATION

This is a continuation-in-part application of U.S. Ser. No. 412,980, filed 26 Sep. 1989, now abandoned.

DESCRIPTION

Technical Field

The present invention relates generally to the detection and isolation of toxin-resistant microbes and the use of such microbes to impart disease-resistance to plants. More particularly, the present invention relates to bacteria capable of degrading the phytotoxin cercosporin for use in producing cercosporin-resistant plant varieties.

BACKGROUND OF THE INVENTION

The fungal genus Cercospora includes several species that incite disease in economically important plants. For example, such species as *C. arachidicola*, *C. zeae-maydis*, and *C. kikuchii* are pathogenic to peanut, corn, and soybean, respectively. *C. beticola* causes sugar beet leaf spot resulting in considerable losses to the sugar beet industry of Europe and North America. This disease reduces tonnage, results in sugar beets with decreased sucrose content, and adversely affects the purity of the juice derived from infected plants. Cercospora species are unusual among plant pathogens due to their ability to attack a vast number and diversity of plant hosts. Additionally, a wide variety of organisms are sensitive to cercosporin including mice, bacteria, fungi and plants (5).

Cercospora species are aerial pathogens. Spores produced by these fungi germinate on the leaf surface and ultimately enter the leaf, e.g. through the stomata. Fungal mycelium then kills leaf cells and causes severe blighting of the leaf tissue by ramifying through the intercellular spaces in leaf tissues (5). Symptom development in infected plants is enhanced by high light intensities (3, 4), suggesting the involvement of light activation of the causative agent.

The phytotoxin cercosporin has been isolated from a number of Cercospora-infected plants and is believed to be a disease-inciting agent in these plants. See, e.g., 1, 7, 8. Previous methods of isolation have required several recrystallization steps to assure purity (see 1).

Cercosporin produced by *C. beticola* and other species is a deep red pigment and has the molecular formula $C_{29}H_{26}O_{10}$ and the structure depicted below (16).

The compound is a perylenequinone derivative with an unusual methylenedioxy-containing 7-membered ring. $^{13}$C-labeled sodium acetate precursors are incorporated in a pattern expected for a heptaketide, which subsequently dimerizes (11). When irradiated by light, the toxin produces singlet oxygen and superoxide, believed to cause peroxidation of membrane lipids Membrane damage leads to loss in membrane fluidity, leakage of nutrients and death of the plant cell (5).

Cercosporin is also known to be toxic to bacteria (9). The toxin inhibits growth in both gram-positive and gram-negative organisms, including members of the Bacillus, Clostridium, Pseudomonas and Staphylococcus genera, as well as inhibiting growth of *E. coli* (9). Bacteria and fungi vary in their sensitivity to cercosporin. In general the latter group of organisms are less sensitive than the former. Within the fungi, yeasts and several plant pathogens in the Ascomycete and Deuteromycete classes show resistance to the toxin while isolates of *Neurospora crassa* and several Aspergillus species, although taxonomically related, show sensitivity to the fungal toxin (5). The mechanism for resistance has not been elucidated.

It has not been possible to select for cercosporin-resistant plant cell mutants by mutagenesis and selection with cercosporin in plant tissue cultures (5). Therefore, the development of resistant plant varieties has been hampered. Thus, efforts to control cercosporin-producing fungi heretofore have focused on the application of fungicides, a practice which is costly, environmentally unsound, and has resulted in the development of fungicide-resistant pathogen strains.

It is now known that genes encoding desired proteins can be identified, isolated, cloned and expressed in transgenic organisms, including several important crop plants. One commonly used method of gene transfer in plants involves the use of a disarmed form of the Ti plasmid of the soil bacterium *Agrobacterium tumefaciens* (17). *A. tumefaciens* is a plant pathogen that causes crown-gall tumors in infected plants. Large plasmids, termed Ti- or tumor-inducing plasmids, are responsible for the oncogenicity of the bacterium as well as for the transfer of foreign DNA to the plant. Similarly, *A. rhizogenes* contains Ri- or root-inducing plasmids that induce root growth. Both plasmid types include a vir or virulence region that must be functional in order to transform wild-type cells to tumor cells (6).

Transformation results in the integration of another plasmid portion, termed the T- or transfer-DNA, into the nuclear genome of the transformed cells. Ri and Ti plasmids can be manipulated to allow insertion of foreign DNA, encoding a desired protein, into the T-DNA region. The foreign DNA can be transferred either via a vector bearing both the vir gene and the foreign gene or by a binary vector system consisting of two plasmids, one containing the vir gene and the other carrying the foreign gene. See, e.g., U.S. Pat. No. 4,658,082; Simpson et al. (13). Transformed plant cells can then be regenerated to produce varieties bearing the inserted gene. The production of transgenic, cercosporin-resistant plants will provide a useful and novel approach for the control of Cercospora-induced plant diseases.

DISCLOSURE OF THE INVENTION

The present invention is based on the discovery of bacteria with the ability to degrade the phytotoxin cercosporin. The instant invention is also based on the development of an efficient method of producing cercosporin for use in selection media to both identify cercosporin-resistant bacterial strains and to identify recombinant clones bearing the gene encoding for cercosporin degradation.

In one embodiment, the present invention is directed to a method for purifying cercosporin comprising:

a) providing a source of cercosporin;

b) extracting cercosporin from the cercosporin source into a first organic solvent to give a first cercosporin-containing extract;

c) removing the solvent from the first cercosporin-containing extract;

d) extracting the cercosporin-containing extract of c) into a second organic solvent to give a second cercosporin-containing extract; and e) removing the second organic solvent from the second cercosporin-containing extract to yield a cercosporin-containing residue.

In another embodiment, the invention is directed to a method for purifying cercosporin comprising:

a) culturing *Cercospora beticola* in potato dextrose broth to yield a cercosporin-containing medium;

b) collecting the cercosporin-containing medium;

c) extracting cercosporin from the cercosporin-containing medium with ethanol and in an excess of EDTA to give a first cercosporin-containing extract;

d) filtering and removing the ethanol from the first cercosporin-containing extract to give a cercosporin-containing solution;

e) extracting the cercosporin-containing solution of d) into ethyl acetate to give a second cercosporin-containing extract;

f) removing the ethyl acetate from the cercosporin-containing extract of e) to give a cercosporin-containing residue; and g) crystallizing the cercosporin-containing residue of f) to yield substantially pure cercosporin.

In still another embodiment, the invention is directed to a method for purifying cercosporin comprising:

a) providing a source of cercosporin;

b) extracting cercosporin from the cercosporin source with a basic solution having a pH more than about 11 to give a substantially green, cercosporin-containing extract;

c) filtering the cercosporin-containing extract followed by acidification of the cercosporin-containing extract with an acidic solution having a pH less than about 3, to give a substantially red, acidified extract;

d) extracting the acidified extract into an organic solvent to give a solution containing cercosporin in the solvent;

e) removing the solvent from the solution to yield a cercosporin-containing residue; and f) chromatographing the cercosporin-containing residue on a chromatographic resin that separates substances based on hydrophobicity, to yield substantially pure cercosporin-containing fractions.

In another embodiment, the present invention is directed to a method for isolating and purifying cercosporin comprising:

a) culturing *Cercospora beticola* on potato dextrose agar medium in continuous light, to yield a cercosporin-containing medium;

b) collecting the cercosporin-containing medium;

c) extracting cercosporin from the cercosporin-containing medium with 0.5N NaOH to give a cercosporin-containing extract;

d) filtering the cercosporin-containing extract followed by acidification of the cercosporin-containing extract to about pH 2 with 6N HCl to give an acidified extract;

e) extracting the acidified extract into ethyl acetate to give a solution containing cercosporin in the ethyl acetate;

f) removing the ethyl acetate from the solution to yield a cercosporin-containing residue;

g) chromatographing the cercosporin-containing residue using Sephadex LH 20 and ethanol as an eluant and collecting cercosporin-containing fractions; and h) crystallizing the cercosporin-containing fractions to yield substantially pure cercosporin.

In yet another embodiment, the present invention is directed to a method of identifying a microbe capable of degrading cercosporin comprising:

a) culturing at least one microbe in a first medium containing a known concentration of cercosporin under conditions sufficient to promote growth of colonies of the microbe;

b) identifying colonies which discolor the first culture medium;

c) extracting the discolored medium and determining the concentration of cercosporin present in the discolored medium to determine whether cercosporin is degraded by the microbe.

In still another embodiment, the instant invention is directed to a method of identifying a microbe capable of degrading cercosporin comprising:

a) culturing at least one microbe in a first medium containing cercosporin under conditions sufficient to promote growth of colonies of the microbe;

b) identifying colonies which discolor the first culture medium;

c) subculturing the colonies of step b in a second culture medium containing a known concentration of cercosporin under conditions sufficient to promote growth of the microbe and identifying colonies that discolor the second culture medium;

d) isolating the discolored medium and determining the concentration of cercosporin present in the discolored medium to determine whether cercosporin is degraded by the microbe.

In particularly preferred embodiments, the cercosporin present in the medium used to identify cercosporin-resistant microbes is derived from the purification methods described above.

Another embodiment of the subject invention is directed to a method of identifying a microbe capable of degrading cercosporin comprising:

a) culturing at least one microbe in a medium containing at least about 20 ug of radiolabeled cercosporin per ml of medium, the medium having a known amount of radioactivity per volume of medium and the culturing being done under conditions sufficient to promote growth of colonies of the microbe;

b) identifying colonies that discolor the first culture medium;

c) isolating and extracting the discolored medium with a first organic solvent;

d) fractionating the extract according to hydrophobicity; and e) determining the radioactivity per volume of the various fractions to determine whether cercosporin is degraded by the microbe.

Another embodiment of the present invention is directed to a DNA construct comprising an expression cassette comprised of:

a) a DNA coding sequence for a polypeptide capable of degrading cercosporin; and b) control sequences that are operably linked to the coding sequence whereby the coding sequence can be transcribed and translated in a host cell, and at least one of the DNA coding sequences or control sequences is heterologous to the host cell.

Preferred embodiments of the subject invention include a host cell stably transformed by a DNA construct as described above; and a method of producing a polypeptide of a recombinant gene comprising:

a) providing a population of these host cells; and b) growing the population of cells under conditions whereby the polypeptide encoded by the coding sequence of the expression cassette is expressed.

In yet another embodiment, the present invention is directed to a transgenic plant capable of degrading cercosporin. In another embodiment, the transgenic plant is a sugar beet plant capable of degrading cercosporin.

Another embodiment of the subject invention comprises a method of conferring cercosporin-resistance to a plant substantially without such resistance comprising transferring to the plant an expressible gene encoding a polypeptide capable of degrading cercosporin.

BRIEF DESCRIPTION OF THE FIGURES

FIG. 1 is a schematic representation of the preferred method for the isolation and purification of cercosporin from *C. beticola* according to the present invention.

DETAILED DESCRIPTION

Figure 2:
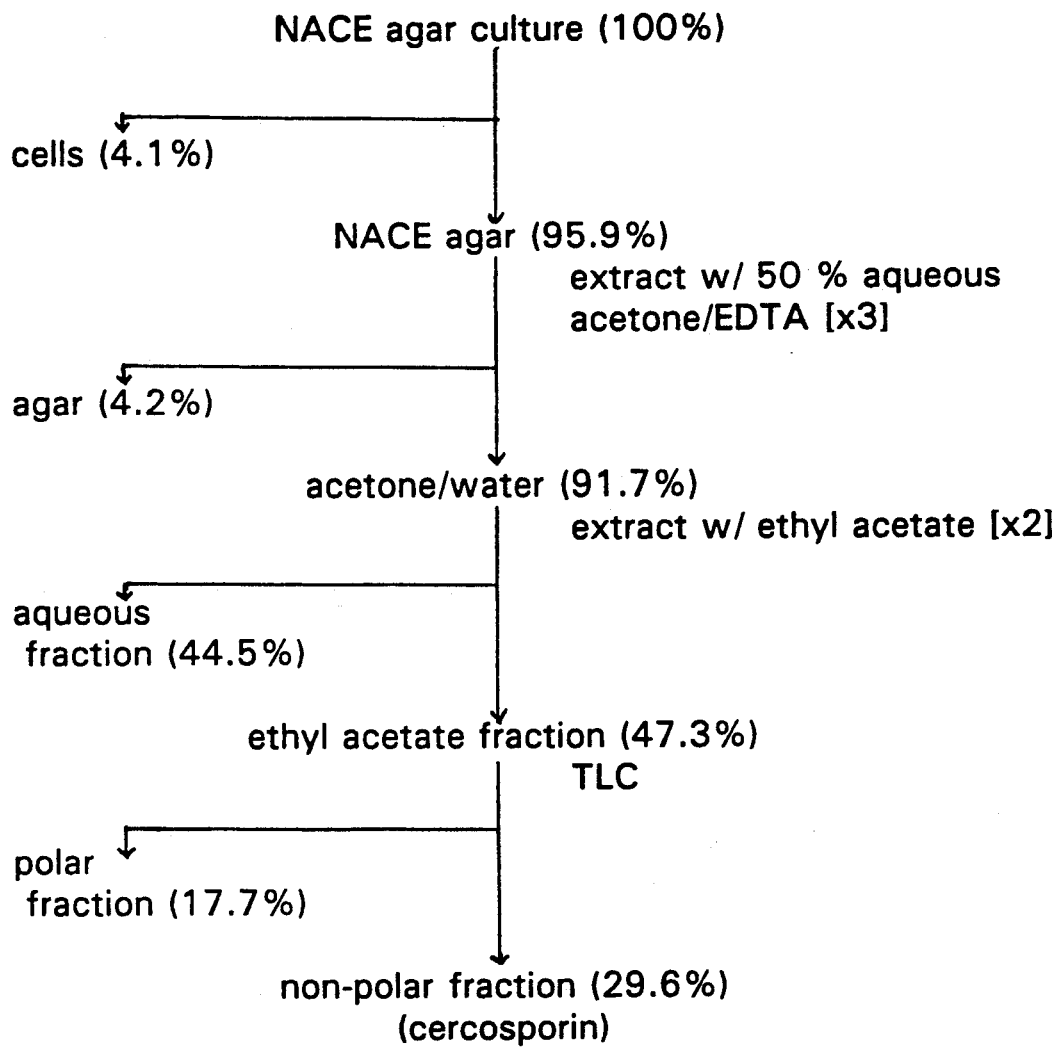
FIG. 2 shows the preferred method for fractionation of radiolabeled cercosporin-containing Nutrient agar after growth and degradation by a cercosporin-resistant bacterial isolate. The numbers in parentheses indicate the total recovered radioactivity in each fraction isolated from Nutrient agar supplemented with cercosporin (NACE) used to grow organism EA4 as described in Example C8. These values represent an average value for colored and discolored agar.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., J. H. Langenheim and K. V. Thimann, *Botany: Plant Biology and Its Relation to Human Affairs* (1982) John Wiley; *Cell Culture and Somatic Cell Genetics of Plants*, Vol. 1 (I. K. Vasil, ed. 1984); R. V. Stanier, J. L. Ingraham, M. L. Wheelis, and P. R. Painter, *The Microbial World*, (1986) 5th Ed., Prentice-Hall; O. D. Dhringra and J. B. Sinclair, *Basic Plant Pathology Methods*, (1985) CRC Press; Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); and the series *Methods in Enzymology* (S. Colowick and N. Kaplan, eds., Academic Press, Inc.).

A. DEFINITIONS

In describing the present invention, the following terms will be employed, and are intended to be defined as indicated below.

By "microbe" is meant any microorganism including both eucaryotic and procaryotic microorganisms, such as fungi, yeasts, bacteria, actinomycetes, algae and protozoa, as well as other unicellular structures capable of growth in culture.

A "cercosporin-producing microbe" is any microbe capable of producing the phytotoxin cercosporin or analogs thereof. Such microbes include but are not limited to members of the fungal genus Cercospora, as well as recombinantly derived organisms which have been genetically altered to enable them to produce cercosporin or analogues thereof.

By "degrading cercosporin" is meant any modification to the cercosporin molecule which causes a decrease or loss in its phytotoxic activity. Such a change can comprise cleavage of any of the various bonds, oxidation, reduction, the addition or deletion of a chemical moiety, or any other change that affects the activity of the molecule.

"Substantially pure" cercosporin refers to a composition including cercosporin and one or more other components wherein cercosporin comprises at least 70%, preferably 80% or more, and most preferably 90-95% or more of the composition. "Substantially pure" also refers to those compositions containing only trace amounts of other components.

By "transgenic plant" is meant any plant or plant cell that has become transformed by the introduction, stable and heritable incorporation, into the subject plant or plant cell, of foreign DNA, i.e. DNA encoding for a protein not normally found within that plant species.

"Plantlet" refers to a plant sufficiently developed to have a shoot and a root that is asexually reproduced by cell culture.

"Explant" refers to a section or piece of tissue from any part of a plant for culturing.

By "hormone" is meant any plant growth regulator that affects the growth or differentiation of plant cells. Such hormones include cytokinins, auxins, and gibberellins, as well as other substances capable of affecting plant cells.

The term "callus" and its plural "calli", refer to an unorganized group of cells formed in response to cutting, severing, or other injury inflicted on plant tissue. Excised pieces of plant tissue and isolated cells can be induced to form callus under the appropriate culture conditions. Callus can be maintained in culture for a considerable time by transferring or subculturing parts of the callus to fresh medium at regular intervals. The transfer of callus to liquid medium leads to dispersion of the tissue and the formation of a plant cell suspension culture. Callus can be induced to undergo organized development to form shoots and roots.

"Embryoid" refers to a structure similar in appearance to a plant zygotic embryo.

"Somatic hybrid" and "somatic hybridization" refers generally to stable combination of cellular material, be it protoplast/protoplast or protoplast/cytoplast combinations, and includes cybrids and cybridization.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at its 3' terminus by the translation start codon (ATG) of a coding sequence and extends upstream (5' direction) to include the minimum number of bases or elements necessary to initiate transcription. Within the promoter sequence will be found a transcription initiation site, as well as protein binding domains responsible for the binding of RNA polymerase. Eucaryotic promoters will often, but not always, contain "TATA" boxes and "CAT" boxes. Procaryotic promoters contain Shine-Dalgarno sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of undergoing transformation, by an exogenous DNA sequence.

A cell has been "transformed" by exogenous DNA when such exogenous DNA has been introduced inside the cell membrane. Exogenous DNA may or may not be integrated into (covalently linked to) chromosomal DNA making up the genome of the transformed cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

A "clone" is a population of cells derived from a single cell or common ancestor by mitosis. A "cell line" is a clone of a primary cell that is capable of stable growth in vitro for many generations.

Two DNA, RNA or polypeptide sequences are "substantially homologous" when at least about 85% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning*, Vols. I & II, supra; *Nucleic Acid Hybridization*, supra.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacterium. Another example of a heterologous coding sequence is a construct where the coding sequence itself is not found in nature (e.g., synthetic sequences having codons different from the native gene). "Heterologous" DNA also refers to DNA not found within the host cell in nature. Allelic variation or naturally occurring mutational events do not give rise to a heterologous region of DNA, as these terms are used herein.

The term "polypeptide" as used herein is used in its broadest sense, i.e., any polymer of amino acids (dipeptide or greater) linked through peptide bonds. Thus, the term "polypeptide" includes proteins, oligopeptides, protein fragments, analogues, muteins, fusion proteins and the like. The term also encompasses amino acid polymers as described above that include additional non-amino acid moieties. Thus, the term "polypeptide" includes glycoproteins, lipoproteins, phosphoproteins, metalloproteins, nucleoproteins, as well as other conjugated proteins. The term "polypeptide" contemplates polypeptides as defined above that are recombinantly produced, isolated from an appropriate source, or synthesized.

B. GENERAL METHODS

The present invention is based on the discovery of bacteria with the ability to degrade the phytotoxin cercosporin and a reliable method of identifying such microorganisms. The instant invention is also based on the discovery of an efficient and reproducible method for isolating and purifying cercosporin from a cercosporin-producing microbe. Cercosporin so isolated can be incorporated into microbial culture media used to screen microbes for their capability of degrading this phytotoxin. Such screening assays, using purified cercosporin, serve a dual purpose. First, new microbial strains able to degrade cercosporin can be identified. Additionally, selection media containing cercosporin can be used to identify recombinant microbial strains that have acquired this capability through genetic transformation.

Thus, DNA encoding a protein able to inactivate cercosporin, can be isolated and cloned in an appropriate vector and inserted into an organism normally sensitive to this toxin. Organisms expressing the gene can be easily identified by their ability to cause discoloration of the medium due to degradation of cercosporin. The protein capable of degrading cercosporin can be isolated and characterized using techniques well known in the art. Furthermore, The gene imparting cercosporin-resistance can be transferred into a suitable plasmid, such as into the T-DNA region of the Ti or Ri plasmid of the soil bacteria *Agrobacterium tumefaciens* or *Agrobacterium rhizogenes*, respectively. Plant tissue can be inoculated with the transformed bacteria. Additionally, plant tissues which have been co-cultivated with Agrobacterium spp. can be incubated in the presence of cercosporin, preferably in the light, to select for cercosporin-resistant transgenic plants, i.e., the gene for cercosporin degradation can serve as a light-sensitive selectable marker. Thus, the inoculated tissue is regenerated to produce cercosporin-resistant transgenic plants.

Due to the broad spectrum of biocidal action of cercosporin as previously noted (see also 5, 18 referenced herein) the gene for cercosporin degradation should offer general applicability in transformation and transfection studies of a wide range of organisms. To date, no light-specific reporter genes are available for transformation studies. Thus, the use of this gene offers a good selectable marker for plant transformation in general.

ISOLATION AND PURIFICATION OF CERCOSPORIN

Cercosporin can be isolated from any of several cercosporin-producing organisms. Such organisms include members of the fungal genus Cercospora, including but not limited to those species listed in Table 1. A particularly preferred organism for use with the present invention is *C. beticola*. This, and other Cercospora species, can be obtained from several commercial sources including the ATCC.

TABLE 1

| Species of Cercospora that Produce Cercosporin |
|---|
| *Cercospora arachidicola* |
| *Cercospora ariminiensis* |
| *Cercospora asparagi* |
| *Cercospora bertoreae* |
| *Cercospora beticola* |
| *Cercospora bizzozeriana* |
| *Cercospora canescens* |
| *Cercospora carotae* |
| *Cercospora chenopodii* |
| *Cercospora cistinearum* |
| *Cercospora cladosporioides* |
| *Cercospora diazu* |
| *Cercospora dulcamarae* |
| *Cercospora erysimi* |
| *Cercospora hayii* |
| *Cercospora kikuchii* |
| *Cercospora malvacearum* |
| *Cercospora malvicola* |
| *Cercospora medicaginis* |
| *Cercospora oryzae* |
| *Cercospora personata* |
| *Cercospora plantaginis* |
| *Cercospora ricinella* |
| *Cercospora setariae* |
| *Cercospora unamunoi* |
| *Cercospora violae* |
| *Cercospora zeae-maydis* |

Generally, the desired fungus is grown axenically on an appropriate solid or suspension medium. Suitable media include Potato Dextrose Agar (PDA), Potato Dextrose Broth (PDB), V-8 Juice agar (V-8) (both described in greater detail in the Experimental section), Raulin-Thom medium, malt extract (16) Sucrose Medium (S) (7), Minimal Medium (MM) (7), Complete Medium (CM) (7), Minimal Medium with Soybean Leaves (SBL) (7), and Sucrose Sorbose Medium (SS) (7), with PDA, PDB and V-8 being particularly preferred. The media used can contain a variety of nitrogen and carbon sources, as well as other nutrients, well known in the art. Generally, the fungus is grown in continuous light at temperatures ranging from 10° C. to 35° C., more usually 20° C. to 30° C. and preferably 24° C. to 26° C. Conditions can be varied so that the fungus can be grown on one medium, subcultured to another medium, and exposed to differing amounts of light and darkness. One of ordinary skill in the art will easily find conditions suited to their needs.

Incubation continues for approximately 1 to 3 weeks, until fungal colonies have attained a diameter of from about 1–5 cm, more preferably 2–3 cm, or if grown in broth, until the medium has attained a pink to red coloration. If grown on agar, the agar will appear pigmented, generally a purplish/red color, due to the presence of cercosporin therein. The color will vary depending on the medium or media used to culture the fungus. The mycelium from the center of each colony is then excised, as well as the agar beneath the mycelium, leaving the perimeter intact to provide a further source of cercosporin. After an additional growth period, more mycelium and agar are excised and combined with any previously collected products and cercosporin purified therefrom as shown in FIG. 1.

Specifically, pigmented agar and mycelium is extracted with a strong base having a pH more than about 11, and preferably within the pH range of 12–14, to give a dark green solution. Useful bases include solutions of NaOH or KOH, with a 0.5N NaOH solution being preferred. The extracted cercosporin solution is then filtered and acidified to pH 2–3 with a strong acid having a pH less than about 3 and preferably in the range of 0–2. An exemplary acid is HCl, with 6N HCl being particularly useful. The acidified extract is substantially red in appearance.

The acidified extract is then partitioned against an organic solvent such as ethyl acetate, until the aqueous phase is no longer red. The organic phase, containing the extracted cercosporin, is then collected and the organic solvent removed, such as by volatilization, to yield a cercosporin-containing residue. This residue is then dissolved in an appropriate reagent, such as ethanol, and chromatographed to eliminate remaining impurities. Particularly suitable is the use of a chromatographic resin that separates substances based on hydrophobicity, such as Sephadex LH 20, using ethanol as the eluant. Fractions appearing red in color are collected and the purity can be determined by qualitative thin layer chromatography. The fractions which contain substantially pure cercosporin are bulked and cercosporin crystallized using any suitable reagent, such as ethanol/water, chloroform/benzene, or acetone. Crystallized cercosporin can be dried and stored at −18° C. for further use.

Alternatively, if the fungus is grown in broth, separation of the mycelium from the culture filtrate is not required. Rather, ethanol is added to the culture together with an excess of a chelating agent, such as the sodium salt of EDTA. The mixture is agitated, the extract filtered and ethanol removed. The extract is partitioned as above, dried and the residue is dissolved in a suitable solvent, such as 70% aqueous ethanol. Cooling and slow evaporation of the solvent yields cercosporin as dark red crystals.

IDENTIFICATION OF MICROBES ABLE TO DEGRADE CERCOSPORIN

Organisms can be screened for their ability to degrade cercosporin using the present method. In this way, plant, soil, marine and fresh water samples can be screened and organisms isolated therefrom that are able to degrade cercosporin. Alternatively, already isolated microbial strains, suspected of possessing this capability, can be screened. Putative cercosporin-resistant bacteria include bacteria associated with plant species susceptible to Cercospora infection. For instance, bacteria associated with the phylloplane of Cercospora-infected peanut as well as other susceptible plant species, might be expected to degrade cercosporin. Furthermore, members of bacterial genera known to be versatile in their catabolism of complex organic molecules, such as members of the genus Pseudomonas, might degrade cercosporin.

Isolated microbial strains, including yeast, fungi, and bacteria, as well as other microbes, can be grown in the presence of purified cercosporin. The media used will depend on the organism being tested. For example, aerobes and yeasts can be grown in Nutrient broth or on Nutrient agar, containing cercosporin. Particularly useful is cercosporin-containing Nutrient agar, termed NACE, and described in more detail below. Fungi can be grown on any number of appropriate cercosporin-containing media including potato dextrose agar and V-8 juice agar, described more fully below. The media can include any number of additional nutrients, salts or other additives, well known in the art.

Generally, media used to culture the above microbes will contain a known amount of cercosporin, i.e. from 10–200 $\mu$g of cercosporin per ml of media, more usually from 40 to 60 $\mu$g per ml of media, and preferably 50 ug of cercosporin per ml of media. Cercosporin imparts a red color to the media. However, when cercosporin is degraded, the media becomes colorless or discolored. The amount of discoloration will depend on the organism being tested and the conditions of incubation. However, red, cercosporin-containing media, will often discolor to colors ranging from pale red, orange, or pale yellow to colorless, or any colors in between due to the degradation of cercosporin. Thus, isolates which discolor or decolorize the media upon which they are grown, are potential cercosporin inactivators and these microbes can be used in further experiments.

The ability of these microbes to degrade cercosporin can be tested by culturing them on fresh cercosporin-containing medium and determining the concentration of cercosporin present in the discolored agar and comparing this amount to the concentration known to be present in the original culture medium. The concentration of cercosporin in the discolored agar can be determined spectrophotometrically. Specifically, cercosporin can be extracted from the discolored medium using an appropriate organic solvent containing a chelating agent which facilitates extraction of cercosporin from agar media. Such solvents include aqueous acetone, ethanol, and methanol with 50% aqueous acetone containing an excess of sodium EDTA being preferred. The absorption of the extract when dissolved in ethanol can be read spectrophotometrically, at 471 nm, and the concentration of cercosporin determined.

Alternatively, the putative cercosporin-degrading microbes can be grown on substrates including $^{14}$C-labeled cercosporin and the counts per minute of the media determined prior to inoculation with the test organism. Isolated microbes can then be cultured on the labeled media, and agar from discolored and colored areas can be excised separately. Cercosporin can be extracted from the excised agar as illustrated in FIG. 2. Specifically, the agar is extracted using an organic solvent, such as one described above. A second extraction can be done using, for example, ethyl acetate, to further fractionate the culture. The counts per minute in the various fractions can be determined. Additionally, counts in the discolored and colored media can be compared to determine whether the discoloration is due to the degradation of cercosporin or due to some other phenomenon.

Those microorganisms capable of degrading cercosporin can be used to purify the protein responsible for inactivating cercosporin. Furthermore, inactivated cercosporin can be isolated from these cultures, such as by growing the organisms on media containing radioactively-labeled cercosporin, tracing the label, and isolating the inactivated toxin for further study. The inactivated cercosporin can be compared to the active compound for its phytotoxicity to known sensitive plant species, such as sugar beet. Such phytotoxicity assays are known in the art. For example, a whole leaf bioassay can be used in which solutions of the active and inactive compound are applied to the leaves of sensitive plants. The leaves may be treated in situ or, alternatively, excised leaves may be used. The relative toxicity of the compounds can be estimated by grading the ensuing damage to the plant tissues and by measuring the size of lesions formed within a given time period. Other known assays can be performed at the cellular level, employing standard tissue culture methodologies e.g., using cell suspension cultures.

Alternatively, cercosporin-degrading organisms can be used to identify and isolate the gene conferring such cercosporin-resistance, termed herein the Dtox gene, which can further be cloned and expressed in a host cell to allow for the production of the gene product for additional characterization. Additionally, the Dtox gene can be inserted into an appropriate vector and used to transform plant cells.

CLONING THE DTOX GENE

Microorganisms demonstrating cercosporin-resistance can be used to create a genomic library using standard techniques, well known in the art. Thus, restriction enzymes can be used to render DNA fragments which can in turn be inserted into any number of suitable cloning vectors. Numerous cloning vectors are known to those of skill in the art, and the selection of an appropriate cloning vector is a matter of choice. The cloning vector need only be capable of transforming a host cell incapable of cercosporin degradation. Examples of recombinant DNA vectors for cloning and host cells which they can transform, shown in parentheses, include the bacteriophage lambda (*E. coli*), pBR322 (*E. coli*), pACYC177 (*E. coli*), pKT230 (gram-negative bacteria), pGV1106 (gram-negative bacteria), pLAFRI (gram-negative bacteria), pME290 (non-*E. coli* gram-negative bacteria), pIJ61 (Streptomyces), pUC6 (Streptomyces), YIp5 (Saccharomyces), and YCp19 (Saccharomyces). See, generally *DNA Cloning*, Vols. I and II, supra; Maniatis et al., supra. Particularly useful is a cloning vector able to transform *E. coli*.

Once the cloning vector has been inserted into an appropriate host cell, the cells are grown on cercosporin containing media and screened for their ability to degrade cercosporin as previously described. Plasmid DNA inserts from colonies which degrade cercosporin are characterized by subcloning, transposon tagging, and DNA sequence analysis, all well within the skill in the art (see, e.g., 10). Once a coding sequence is determined, recombinant protein molecules able to degrade cercosporin can be produced according to the present invention by constructing an expression cassette and transforming a host cell therewith to provide a cell line or culture capable of expressing the desired protein which is encoded within the expression cassette.

Sequences encoding the Dtox gene can be either prepared directly by synthetic methods based on the determined sequence, or by using the sequence to design oligonucleotide probes to clone the coding sequence using known techniques. The oligonucleotide probes can be prepared and used to screen a DNA library from an organism able to degrade cercosporin as determined above. The basic strategies for preparing oligonucleotide probes and DNA libraries, as well as their screening by nucleic acid hybridization, are well known to those of ordinary skill in the art. See, e.g., *DNA Cloning,* Vol. I, supra; *Nucleic Acid Hybridization,* supra; *Oligonucleotide Synthesis,* supra; Maniatis et al., supra.

The coding sequence can be comprised entirely of the Dtox coding sequences, or such sequences can be fused to other sequences (e.g., leader sequences) so that a fusion protein is encoded. See, e.g., U.S. Pat. Nos. 4,431,739; 4,425,437; 4,338,397. Once an appropriate coding sequence for the cercosporin-degrading protein has been prepared or isolated, it can be cloned into any suitable vector or replicon, known in the art. These vectors are described above, with *E. coli* being the host bacterium particularly preferred.

To complete construction of the expression cassettes, the coding sequence is then operably linked to control sequences such as a promoter, ribosome binding site (for bacterial expression) and, optionally, an operator, so that the DNA sequence encoding the protein is transcribed into messenger RNA in the host cell transformed by the vector containing the expression construction. It is within the skill of the art to operably link the cercosporin-degrading coding sequence to appropriate control sequences in order to bring about transcription and translation. In general, the coding sequence will be downstream from the promoter sequence and any expression regulatory regions, such as enhancers or operator sequences. If the coding sequence is linked to a heterologous coding sequence or start codon, then it is important to place the coding sequence in reading frame with the latter. If the intended expression host is procaryotic, then it will also be necessary to include a ribosome binding site among the upstream control sequences. Downstream operably linked control sequences will usually comprise a transcription termination sequence.

The construct can then be inserted into an appropriate expression vector. A number of procaryotic and eucaryotic expression vectors are known in the art. Preferred vectors are procaryotic expression vectors which are sensitive to cercosporin. A particularly preferred host for such vectors is *E. coli*. The cercosporin-degrading protein is then produced by growing the host cells transformed by the expression cassette under conditions which cause the expression of the biologically active protein, as indicated by the host cells ability to degrade cercosporin in the medium on which it is grown, as described above. The protein can be isolated from the host cells and purified for further study. If the protein is not secreted, it may be necessary to disrupt the host cells and purify the protein from the cellular lysate. Various purification techniques, such as HPLC, size-exclusion chromatography, electrophoresis, and immunoaffinity chromatography, are known, and the selection of the appropriate purification and recovery method is within the skill of the art.

Similarly, the Dtox gene can be inserted into the T-DNA region of a Ti or Ri plasmid derived from *A. tumefaciens* or *A. rhizogenes,* respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., reference (2). Particularly suitable control sequences for use in these plasmids are promoters for constitutive leaf-specific expression of the Dtox gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; co-owned pending U.S. application Ser. No. 913,914, filed Oct. 1, 1986; Simpson et al. (13); all incorporated by reference in their entirety.

Once constructed, these plasmids can be placed into *A. rhizogenes* or *A. tumefaciens* and these vectors used to transform cells of plant species which are ordinarily susceptible to Cercospora infection. For example, sugar beet (*Beta vulgaris*) is often plagued with such infection and resistant sugar beet crops could be developed to withstand Cercospora-induced disease. Several other transgenic plants are contemplated by the present invention including but not limited to soybean, peanut, corn, sorghum, alfalfa, rice, clover, cabbage, banana, coffee, celery, tobacco, cowpea, cotton, sesame, and mung bean, all of which are known to be attacked by Cercospora. The selection of either *A. tumefaciens* or *A. rhizogenes* will depend on the plant being transformed thereby. In general *A. tumefaciens* is the preferred organism for transformation. Most dicotyledons, some gymnosperms, and a few monocotyledons (e.g. certain members of the Liliales and Arales) are susceptible to infection with *A. tumefaciens. A. rhizogenes* also has a wide host range, embracing most dicots and some gymnosperms, which includes members of the Leguminosae, Compositae and Chenopodiaceae. Alternative techniques which have proven to be effective in genetically transforming plants include particle bombardment and electroporation. See e.g. 19, 20, 21 and 22.

Once transformed, these cells can be used to regenerate transgenic plants, capable of degrading cercosporin. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors and cultured under conditions which promote plant regeneration. Roots or shoots transformed by inoculation of plant tissue with *A. rhizogenes* or *A. tumefaciens,* containing the Dtox gene, can be used as a source of plant tissue to regenerate cercosporin-resistant transgenic plants, either via somatic embryogenesis or organogenesis. Examples of such methods for regenerating plant tissue are disclosed in Shahin (12); U.S. Pat. No. 4,658,082; Simpson et al. (13); co-owned pending U.S. patent application Ser. Nos. 913,913 and 913,914, both filed Oct. 1, 1986; the entire disclosures therein incorporated herein by reference.

Described below are examples of the present invention which are provided only for illustrative purposes. The examples are not intended to limit the scope of the present invention in any way, as numerous embodiments within the scope of the claims will be apparent to those of ordinary skill in the art in light of the present disclosure. Those of ordinary skill in the art are presumed to be familiar with (or to have ready access to) the reference cited in the application, and the disclosures thereof are incorporated by reference herein.

C. EXPERIMENTAL

C1. Isolation and Purification of Cercosporin

C1.a. Cercosporin was purified from *Cercospora beticola*, ATCC No. 24080 using the following method. *C. beticola* was cultured on standard V-8 juice agar having the following formula:

| V-8 juice | 200 ml (Campbell Soup Co.) |
|---|---|
| CaCO$_3$ | 3 g |
| Agar | 15 g |
| Tap H$_2$O to | 1 l (pH adjusted to 7.2) |

The culture was incubated under continuous light at 25° C. in 20 mm×100 mm plastic Petri plates for a total period of 14–21 days. Fungal growth was associated with the production of a purple/red pigment. Fungal growth was transferred as approximately 3 mm$^2$ agar plugs to several sites on fresh V-8 juice agar or to PDA (Difco). The subcultured fungus was grown at 25° C. under continuous illumination (50–300, μEinsteins. m$^{-2}$.S$^{-1}$) supplied by F20T12/CW Cool White fluorescent strip lights. When the fungal colonies attained a diameter of approximately 2.5 cm, the center of each colony, both mycelium and agar, was excised for extraction of cercosporin, leaving the perimeter of the colony intact as a source of further growth with the concomitant production of cercosporin. These colonies were incubated for a total of approximately 3 weeks, after which time mycelium and pigmented agar were again excised and added to the previously excised products. Colorless agar was discarded.

Cercosporin was then extracted from the collected agar as follows. The pigmented agar excised above was diced into approximately 3 mm cubes. The diced agar (100–150 ml volume per batch) was extracted 3 times with 2 volumes of 0.5N NaOH to give a dark green solution. The NaOH extracts were bulked, filtered, and acidified with 6N HCl to pH 2.0, to form a red solution. The acidified extract was partitioned against ethyl acetate, rendering a red organic phase. Extraction into the ethyl acetate solution continued until the aqueous phase was no longer red. The cercosporin-containing ethyl acetate solution was then dried over anhydrous magnesium sulfate and the solvent removed, in vacuo, at a temperature not exceeding 40° C. The dried residue was dissolved in a small volume of ethanol and applied to a Sephadex LH 20 column, 2.5 cm i.d.×45 cm long using ethanol, delivered from a gravity-feed reservoir, as the eluant. The eluate was collected using a fraction collector. Cercosporin-containing fractions were bright red.

The purity level of these fractions was determined by qualitative thin layer chromatography on silica gel plates with chloroform, methanol and water at a ratio of 35:12:2, as the developing solvent. The cercosporin-containing fractions were pooled and cercosporin crystallized therefrom using ethanol/water (8:1) at approximately 4° C. Cercosporin crystals were dried and stored at −18° C. for further use.

C1.b. The following alternative procedure was used to purify cercosporin. *C. beticola* (C-7), (from the USDA), was cultured in 100–400 ml volumes of Potato Dextrose Broth (PDB) in 250–1000 ml Erlenmeyer flasks.

The cultures were incubated with a 14:10 photoperiod at 25° C. for 7–14 days. The medium became pink and intensified to a red color as incubation, and thus cercosporin production, proceeded.

Ethanol (1.5 volumes) was added to the culture, together with an excess of sodium EDTA. Sodium EDTA is considered present in excess when solid EDTA salt is present due to saturation of the solution. The culture was agitated on a gyratory shaker for one hour and the extract filtered. Ethanol was removed under vacuum at approximately 40° C. The extract was partitioned against ethyl acetate and dried as in Example C1.a. The residue from the dried ethyl acetate extract was dissolved in a small volume of 70% aqueous ethanol. A beaker containing the solution was placed in a fume hood and the ethanol was allowed to evaporate. This procedure yielded fine, dark red crystalline needles of cercosporin.

C2. Preparation of $^{14}$C-Labeled Cercosporin for Incorporation into Culture Media $^{14}$C-labeled cercosporin was prepared in the following manner. 2.5 ml of an ethanolic solution of uniformly labeled $^{14}$C sodium acetate (New England Nuclear) (approximately 50 mCi/mMol, 250 uCi) was dried in a vial under a stream of nitrogen gas. The residual solid sodium acetate was dissolved in 750 ul of sterile water. Three 50 ul aliquots of this solution were applied at separated sites to the surface of each of five Petri plates (100×20 mm) of PDA, and the liquid was allowed to be taken up by the medium. Agar plugs taken from a 12 day culture of *C. beticola* (ATCC No. 24080) grown on PDA were placed on the medium at the sites of application of the sodium acetate solution. The organism was incubated at 25° C. under continuous illumination, and the fungal colonies were harvested sequentially from their centers, after 8, 12, and 16 days, as described in Example C1. The harvested agar was bulked (33.25 g wet weight) and extracted as described above in Example C1.

The dried crude cercosporin fraction was dissolved in ethanol for purification by thin layer chromatography, using silica gel thin layer plates, developed in chloroform, methanol, and water, at a ratio of 35:12:2. Cercosporin was eluted from the silica gel with acetone, the acetone was evaporated, and the residue dissolved in ethanol for quantification from its extinction at 471 nm. The yield was 1.82 mg. Radioactivity of the $^{14}$C-labeled cercosporin was determined by liquid scintillation counting of a small aliquot. The material had a specific activity of 1.91 mCi/mMol.

C3. Preparation of NACE Culture Medium for use in the Screening and Selection of Microbes Capable of Degrading Cercosporin Nutrient agar containing cercosporin, termed NACE, was prepared in the following manner. Crystalline cercosporin prepared as in Experiment C1 was dissolved in 0.1N NaOH to give a concentration of 10 mg of cercosporin per ml of solution. 5 ml of 0.1N HCl per liter of medium was added to molten, sterile nutrient agar (Difco). 5 ml of the cercosporin solution was then added per liter of the molten, sterile nutrient agar/HCl, to yield a final cercosporin concentration of 50 ug per ml of medium. The molten medium was mixed by gentle swirling and aseptically dispensed into 100 mm×25 mm plastic Petri plates, at a volume of 25 ml per plate. The agar was allowed to gel at ambient temperature, condensed water within the dish permitted to evaporate, and the dishes stored at 4° C. in the dark. The plates had a distinctive, uniform red coloration due to the presence of cercosporin.

C4. Enrichment of Mixed Bacterial Populations Prior to Screening and Selection of Microbes Capable of Degrading Cercosporin Mixed bacterial populations from Cercospora-infected sugar beet plants were obtained as follows.

a) Soil. Soil adhering to the root system of the sugar beet plants after unearthing the plants was removed with a spatula and an aliquot stored in a capped scintillation vial.

b) Leaf surfaces. Leaf surfaces bearing necrotic spots were rubbed with cotton swabs moistened in 0.9% sterile saline. Bacteria and other material was dislodged from the swab by swirling in a small volume of sterile saline. An aliquot of the resulting turbid suspension was added to 5 g of sterile soil in a scintillation vial.

c) Leaf tissue. Pieces of leaf tissue bearing necrotic leaf spots were disrupted in sterile 0.9% saline using a tissue homogenizer. An aliquot of the resulting suspension was added to sterile soil as in b above.

The moisture content of each sample was adjusted to 20% water by weight. Cercosporin, purified as in C1, was added to each soil sample as a solution in 0.1N NaOH, at a concentration of 1 mg cercosporin per 5 g of soil. Amphotericin B was also added at a concentration of 3.5 ug/ml to suppress the growth of eukaryotic organisms. Samples were incubated in the dark at 25° C. Additional purified cercosporin was added as a solution in 0.1N NaOH at a concentration of 1 mg cercosporin per 5 g of soil at approximately 2 week intervals. Moisture content was readjusted to 20% water with each addition of cercosporin. pH was checked to ensure that no major deviations from neutrality occurred in the soil samples.

C5. Initial Screening and Selection of Cercosporin-Resistant Microorganisms

The samples from C4 were screened for their ability to degrade cercosporin using the following method. 0.1 grams of enriched soil from C4 was suspended in 10 ml of sterile 0.9% saline. Serial logarithmic dilutions of the soil suspension were prepared to $10^{-3}$ using sterile 0.9% saline. 50 ul of each dilution was plated on Nutrient agar containing amphotericin B at a concentration of 3.5 ug/ml. Plates were incubated at 25° C. for one to several days until bacterial growth was evident as macroscopic colonies. Plates which contained a suitable number of bacterial colonies were replica plated to NACE medium, made as described in Example C3.

The plates were incubated at 25° C. in the dark. Bacterial isolates which grew to form a colony were scrutinized for any localized color changes caused to the otherwise red medium. Several candidate isolates were observed which caused discoloration or decolorization of NACE medium. These isolates were named EA4, 9.0.H, 9.1 and 1.13. The candidates were streaked on fresh NACE medium to obtain pure cultures. Characteristics for these isolates are given in Table 2. As can be seen, EA4, 9.0.H, and 1.13 were gram-positive and 9.1 gram-negative. Furthermore, EA4 and 9.0H showed an initial, reversible discoloration of the medium. However, after an extended period of time, cercosporin-degradation became irreversible. These isolates have been identified as indicated in Table 2.

TABLE 2

Characteristics of Candidate Bacterial Isolates for Cercosporin Degradation from Example C5

| Isolate/Strain | Gram reaction | Initial reversible degradation | Identity | Source |
|---|---|---|---|---|
| EA4 | + | + | *Bacillus thuringiensis*[a] | garden soil |
| 9.0.H | + | − | Microbacterium sp.[b] | infected sugar beet leaf |
| 9.1 | − | + | *Pseudomonas fluorescens* biovar V[c] | infected sugar beet leaf |
| 1.13 | + | − | *Bacillus subtilis*[a] | garden soil |

[a]Identified by Microbial I.D. Inc., Newark, DE.
[b]Tentative identification by ATCC Identification Service.
[c]Identified by ATCC Identification Service.

The isolates were then transferred to fresh NACE medium by spot-inoculation and their ability to degrade cercosporin determined by the procedure in C6 below. Candidate bacterial isolates were transferred to a preservation medium for long term storage at −80° C.

C6. Assay for Identification of Cercosporin-Degrading Microbes

The candidate bacterial isolates from C5 which discolored or decolorized the cercosporin-containing medium were assayed for their ability to degrade cercosporin using the following method. Agar plugs were removed with a number 2 cork borer from discolored and non-discolored zones beneath and adjacent to the bacterial colonies, and from zones of the Petri plate distant from the bacterial growth. Plugs were also removed in the same manner from uninoculated (control) plates. All Petri plates contained the same volume of NACE agar as described in Example C3. The three different types of agar plugs were separately and thoroughly extracted in 50% aqueous acetone containing an excess of sodium EDTA. The amount of cercosporin present in the agar plugs was determined by reading the absorption of the extract spectrophotometrically at 471 nm, after scanning from 200–600 nm. The amount of cercosporin present in agar plugs taken from the discolored section of the plate was more than 50% lower than that in the control plugs taken from colored NACE medium in the case of isolate EA4. A decrease in the amount of cercosporin extracted from discolored NACE medium, as compared with control NACE medium, was confirmed by qualitative thin layer chromatography (TLC) using the TLC procedure described in Example C1.

C7. Isolation, Culture and Preservation of Bacterial Isolate EA4

A bacterial isolate named EA4 was determined to have the ability to degrade cercosporin using the following technique. Ten grams of a garden soil sample were transferred to a glass scintillation vial. The soil sample was enriched by the addition of 1 mg of cercosporin, purified as in C1, in 4 ml of nutrient broth. The sample was incubated at 26° C. An additional 0.5 mg of purified cercosporin was added after 18 and 22 days. The sample was incubated for an additional 12 days after which time a 0.1 g aliquot of soil was taken and added to 10 ml of sterile saline. 50 ul of this suspension was plated on Nutrient agar supplemented with amphotericin B at a concentration of 3.5 mg/l. The plates were incubated at 25° C. overnight after which time a large number of morphologically diverse bacterial colonies could be seen.

Representatives of 6 different colony types were subcultured on NACE medium prepared as described in Example C3. After incubation for 3 days at 26° C., one of these, designated EA4, clearly showed decoloration of the cercosporin-containing medium. Decoloration of the medium was observed as a distinct pale yellow halo, approximately 4 mm in diameter, around the colony. This colony was streaked on fresh NACE medium to obtain single colonies which provided an axenic culture. Bacteria grown on this medium were used in cercosporin assays as described in C6 with similar results to those reported in C6. A single colony of isolate EA4 growing in NACE was used to inoculate Palleroni and Doudoroff basal medium supplemented with 0.1% yeast extract. The broth culture was incubated at 22° C. on a gyratory shaker. Broth cultures of EA4 were used as inoculum to preserve this isolate at −80° C. in a mixture of DMSO and glycerol.

The EA4 isolate was determined by microscopic examination to be a gram-positive-staining bacillus. Further analysis by Microbial I.D., Inc. (Newark, Del.) demonstrated that isolate EA4 was a member of the genus Bacillus, and most probably was a strain of *B. thuringiensis*.

C8. $^{14}$C-Cercosporin-Degradation Assay using Bacterial Isolate EA4

Further studies were done with the EA4 isolate from Example C7 using $^{14}$C-labeled cercosporin. Cercosporin was radioactively labeled as described in Experiment C2, however the final product after dilution with nonlabeled cercosporin had a specific activity of 26.75 uci/mMol. Thus, 17.5 ug of labeled cercosporin was diluted with nonlabeled cercosporin at a ratio of 1.0:71.4 before addition to molten Nutrient agar, to give a cercosporin concentration of 50.7 ug/ml and approximately 100,000 cpm per 25 ml of NACE.

Two radiolabeled NACE plates were inoculated at multiple sites with isolate EA4 and incubated at 25° C. for 8 days. Bacterial cells were removed from the plates and determined to account for only a small fraction, 4.1%, of the total radioactivity. Agar from the discolored and colored areas of the plates was excised (22 ml and 27 ml, respectively), and fractionated separately by the method depicted in FIG. 2.

Specifically, the agar was first extracted three times with 50% aqueous acetone containing EDTA. The aqueous acetone extract was further extracted two times with ethyl acetate. Table 3 depicts the amount of radioactivity present in the aqueous and ethyl acetate fractions derived from discolored and colored agar on a per unit volume of agar basis. As can be seen, the level of radioactivity in the ethyl acetate fraction is much less in the case of discolored agar as compared with the colored agar, indicating that the $^{14}$C-labeled cercosporin has been degraded.

TABLE 3

| Amount of Radioactivity in Ethyl Acetate and Aqueous Fractions Derived from Discolored and Colored Agar of Cultures of Bacterial Isolate EA4 Grown on Nutrient Agar Supplemented with $^{14}$C cercosporin | | |
|---|---|---|
| | Radioactivity (cpm/ml of agar) | |
| Fraction | Discolored agar | Colored agar |
| ethyl acetate | 893 | 2,027 |
| aqueous | 1,382 | 1,455 |

The ethyl acetate extracts were separated by TLC into nonpolar (cercosporin) and polar fractions, and the amount of radioactivity associated with each fraction recorded. As can be seen in Table 4, in the case of discolored agar, the radioactivity was divided approximately equally between the cercosporin-containing fraction and the polar fraction, while in colored agar, the majority of the radioactivity was in the non-polar cercosporin-containing fraction. The presence of 27% of the cpm in the polar fraction of the colored agar is probably due to diffusion of cercosporin degradation products from the areas of discolored agar. Only 11.2% of the total radioactivity originally present in the discolored agar was recovered as cercosporin. Recovery of radiolabeled cercosporin from an uninoculated control NACE plate with the same specific activity and concentration of cercosporin as inoculated plates was at least 80%, indicating that cercosporin had been degraded in the discolored agar.

TABLE 4

| Percentage of Radioactivity in Polar and Nonpolar Fractions Derived from Ethyl Acetate Extracts of Discolored and Colored Agar of Cultures of Bacterial Isolate EA4 as Determined by Radio-TLC | | |
|---|---|---|
| Agar | Discolored Agar | Colored |
| Polar fraction | 49 | 27 |
| Nonpolar fraction (cercosporin) | 51 | 73 |

C9. Characterization of *Xanthomonas campestris* pv. betae as a Cercosporin Degrader

*X. campestris* pv. betae was purchased from the Plant Disease Division, DSIR, Auckland, New Zealand. This strain was originally isolated from leaf spots of *Beta vulgaris* from Brazil in 1973 and is designated culture number 8917 of the International Collection of Microorganisms from Plants (ICMP). The bacterium was grown initially on nutrient broth. Serial dilutions from a 24 hour Nutrient broth culture were plated on nutrient agar. The 1:100 million dilution plate was replica plated to NACE medium. A single colony from the replica plate was selected and transferred to a fresh NACE plate. After incubation in the dark at 25° C. for 3 weeks, the agar beneath the bacterial colony was decolorized. Analogous procedures with two other ICMP bacterial strains which were also originally isolated from *Beta vulgaris* indicated that they did not degrade cercosporin.

Agar from the discolored and colored portion of the plate was extracted as in C6. The extract obtained from the agar which was in contact with the bacteria was essentially colorless while that from the agar on the same plate that was not in contact with the bacteria was red. Spectrophotometric analysis in the visible region of the spectrum confirmed that the extract of the decolorized agar was deficient in cercosporin as compared with the control extract. An equivalent volume of agar taken from beneath a colony of a Pseudomonas isolate, which did not decolorize NACE medium, was extracted and found to yield cercosporin at the same level as the control extract.

Thus, methods for the purification and use of cercosporin to identify cercosporin-resistant microbes are disclosed as well as techniques for producing transgenic plants capable of degrading cercosporin. Although preferred embodiments of the subject invention have been described in some detail, it is understood that obvious variations can be made without departing from the spirit and the scope of the invention as defined by the appended claims.

References (1) Assante, G., et al. (1977) Phytochemistry 16:243-247.

(2) Benfey, P. N., and Chua, N. H. (1989) Science 244: 174-181.

(3) Calpouzos, L. (1966) Ann. Rev. Phytopathol. 4: 369-390.

(4) Calpouzos, L. (1967) G.F. Phytopathology 57:799-800.

(5) Daub, M. E. (1987) "The Fungal Photosynthesizer Cercosporin and Its Role in Plant Disease in Light-Activated Pesticides" (Ed. J. R. Heitz & K. R. Downum), pp.271-280. Am. Chem. Soc., Washington, D.C.

(6) Hoekema et al. (1983) Nature 303:179-180.

(7) Jenns, A. E., et al. (1989) Phytopathology 79: 213-219.

(8) Kuyama, S., and Tamura, T. (1957) J. Am. Chem. Soc. 79:5725-5726.

(9) Lynch, F. J., and Geoghegan, M. J. (1979) Trans. Br. Mycol. Soc. 72:31-37.

(10) Napoli, C., and Staskawicz, B. (1987) J. Bact. 169:572-578.

(11) Okubo et al. (1975) Agric. Biol. Chem. 39:1173-1175.

(12) Shahin, E. A. (1985) Theor. Appl. Genet. 69:235-240.

(13) Simpson, R. B., et al. (1986) Plant Mol. Biol. 6: 403-415.

(14) Stavely, J. R., and Nimmo, T. A. (1968) Phytopathology 58:1372-1376.

(15) Trulson, A. J., and Shahin, E. A. (1986) Plant Science 47:35-43.

(16) Yamazaki, S., and Ogawa, T. (1972) Agric. Biol. Chem. 36:1707-1718.

(17) Zambryski et al. (1983) EMBO J 2:2143-2150.

(18) Yamazaki, S., Okubo, A., Akiyama, Y., Fuwa, K. (1975) Agric. Biol. Chem. 39:287-288.

(19) Rhodes, C. A., et al. (1988) Science 240, 204-207.

(20) Shigekawa, K. and Dower, W. J. (1988) BioTechniques 6, 742-751.

(21) Sanford, J. C., et al. (1987) Particulate Science & Technology 5:27-37.

(22) McCabe, D. E. (1988) BioTechnology 6:923-926.

We claim:

1. A method of identifying a microbe capable of degrading cercosporin comprising:
    a) culturing at least one microbe in a first agar medium containing a known concentration of cercosporin under conditions sufficient to promote growth of colonies of said microbe;
    b) identifying colonies which discolor said first agar medium;
    c) extracting the discolored medium and determining the concentration of cercosporin present in said discolored medium to determine whether cercosporin is degraded by said microbe, thereby identifying whether said microbe is capable of degrading cercosporin.

2. The method of claim 1 further comprising subculturing said colonies of step b) in a second agar medium containing a known concentration of cercosporin under conditions sufficient to promote growth of said microbe and identifying colonies that discolor said second agar medium said subculturing being done prior to step c).

3. The method of claim 1 wherein said first agar medium and said second agar medium comprise nutrient agar.

4. The method of claim 1 wherein the concentration of cercosporin in said first agar medium and said second agar medium is at least about 20 μg cercosporin per ml of medium.

5. The method of claim 1 wherein the concentration of cercosporin present is determined by extracting the discolored medium using an organic solvent and spectrophotometrically reading the absorbance of the extract at about 470 nm.

6. The method of claim 5 wherein the organic solvent is aqueous acetone containing an excess of a chelating agent.

7. A method of identifying a microbe capable of degrading cercosporin comprising:
    a) culturing at least one microbe in a first agar medium containing cercosporin under conditions sufficient to promote growth of colonies of said microbe;
    b) identifying colonies which discolor said first agar medium;
    c) subculturing said colonies of step b) in a second agar medium containing a known concentration of cercosporin under conditions sufficient to promote growth of said microbe and identifying colonies that discolor said second agar medium;
    d) isolating the discolored medium and determining the concentration of cercosporin present in said discolored medium to determine whether cercosporin is degraded by said microbe, thereby identifying whether said microbe is capable of degrading cercosporin.

8. A method of identifying a microbe capable of degrading cercosporin comprising:
    a) culturing at least one microbe in an agar medium containing at least about 20 μg of radiolabeled cercosporin per ml of medium, said medium having a known amount of radioactivity per volume of medium and said culturing being done under conditions sufficient to promote growth of colonies of said microbe;
    b) identifying colonies that discolor said first agar medium;
    c) isolating and extracting the discolored medium with a first organic solvent; and d) determining the radioactivity per volume of medium present in the extract of c) to determine whether cercosporin is degraded by said microbe, thereby identifying whether said microbe is capable of degrading cercosporin.

9. The method of claim 8 wherein said radiolabeled cercosporin is $^{14}C$-labeled cercosporin and said radioactivity is expressed as counts per minute.

10. The method of claim 8 further comprising extracting the extract from step c) with a second organic solvent.

11. The method of claim 9 wherein said first organic solvent is aqueous acetone containing a chelating agent and said second organic solvent is ethyl acetate.

* * * * *